United States Patent [19]

Leverette

[11] Patent Number: 4,665,907

[45] Date of Patent: May 19, 1987

[54] APPARATUS FOR INHIBITING DIGIT SUCKING

[76] Inventor: Charles R. Leverette, 130 Misty Hollow Way, Woodstock, Ga. 30188

[21] Appl. No.: 807,837

[22] Filed: Dec. 11, 1985

[51] Int. Cl.⁴ ............................ A61F 5/37; A61F 5/50
[52] U.S. Cl. ...................................... 128/133; 128/136
[58] Field of Search .............................. 128/133, 136

[56] References Cited

U.S. PATENT DOCUMENTS

| | | | |
|---|---|---|---|
| 1,584,999 | 5/1926 | Thompson | 128/133 |
| 1,733,933 | 10/1929 | Beltz | 128/133 |
| 1,800,755 | 4/1931 | Roberts et al. | 128/133 |
| 1,944,752 | 1/1934 | Maish | 128/133 |
| 2,536,633 | 1/1951 | Fitch | 128/133 |
| 2,684,065 | 7/1954 | Umbenhower | 128/133 |

Primary Examiner—Robert A. Hafer
Assistant Examiner—Kathleen J. D'Arrigo
Attorney, Agent, or Firm—Jones & Askew

[57] ABSTRACT

Apparatus for attaching to the thumb or finger to inhibit thumb sucking. A bracelet fits around the wrist, and a primary ring attaches to the bracelet. The primary ring is supported by two or more tabs extending outwardly from the ring to the bracelet, and cross-tabs extend between the outward tabs to prevent unwanted withdrawal of the thumb from the ring. A separate booster ring is optionally attached to the primary thumb-encircling ring, providing additional hindrance to thumb sucking.

13 Claims, 6 Drawing Figures

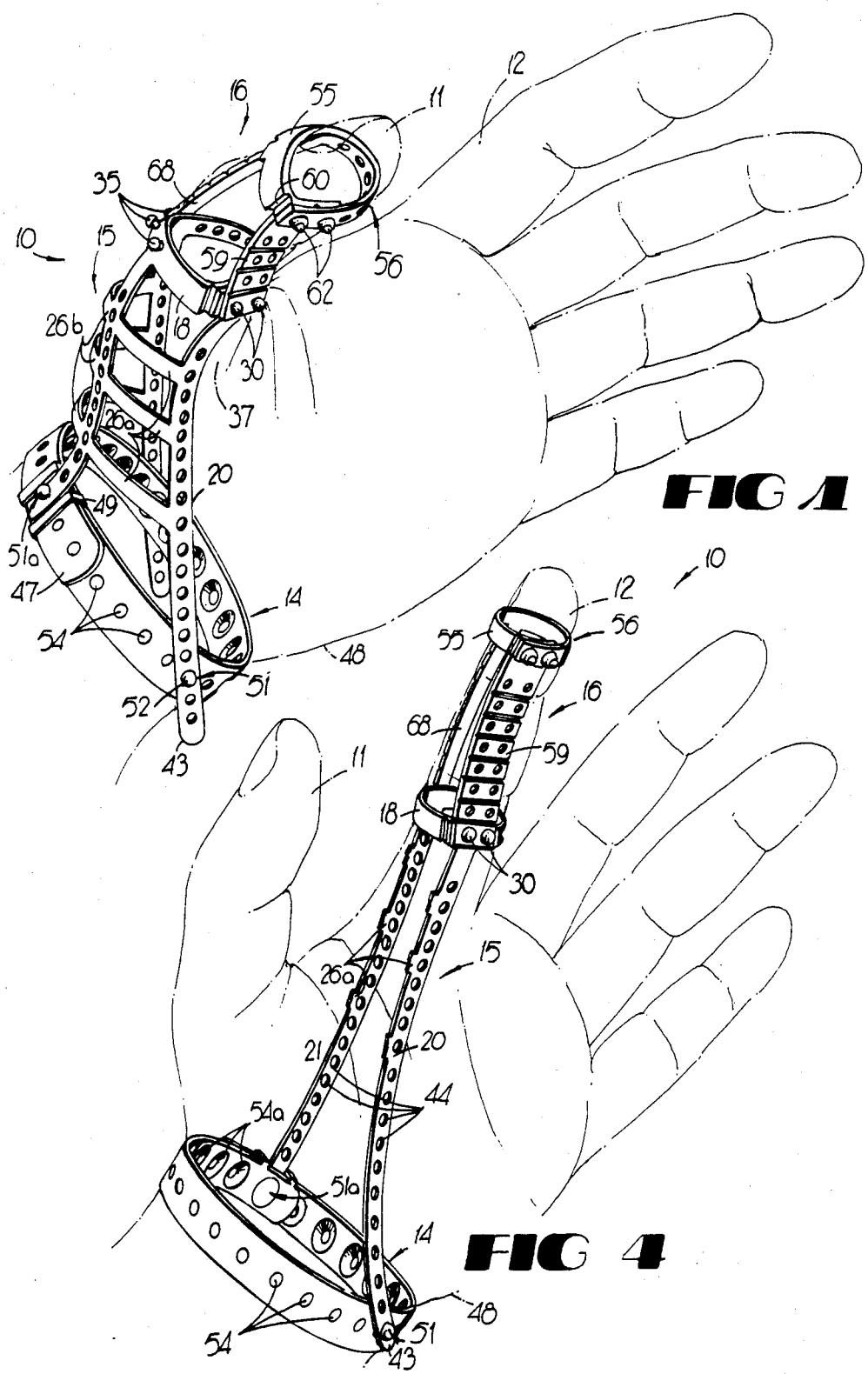

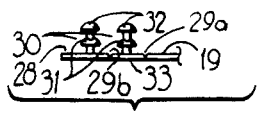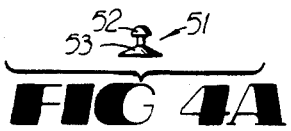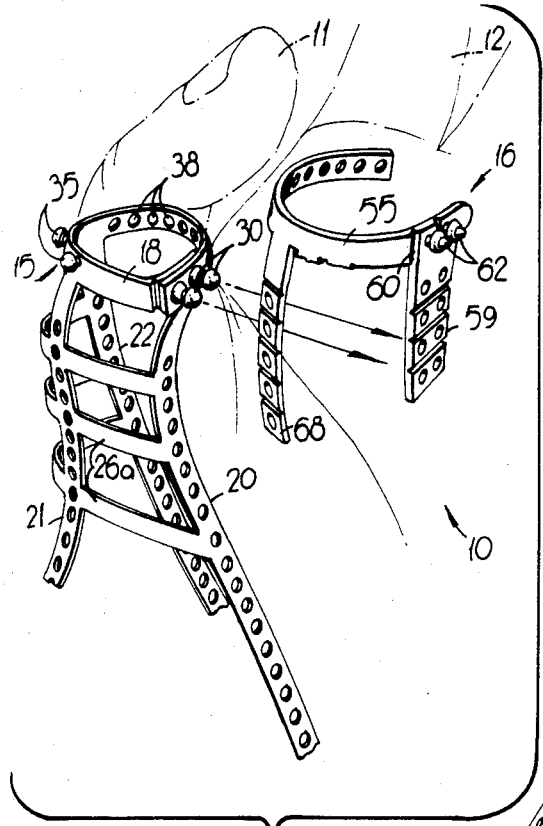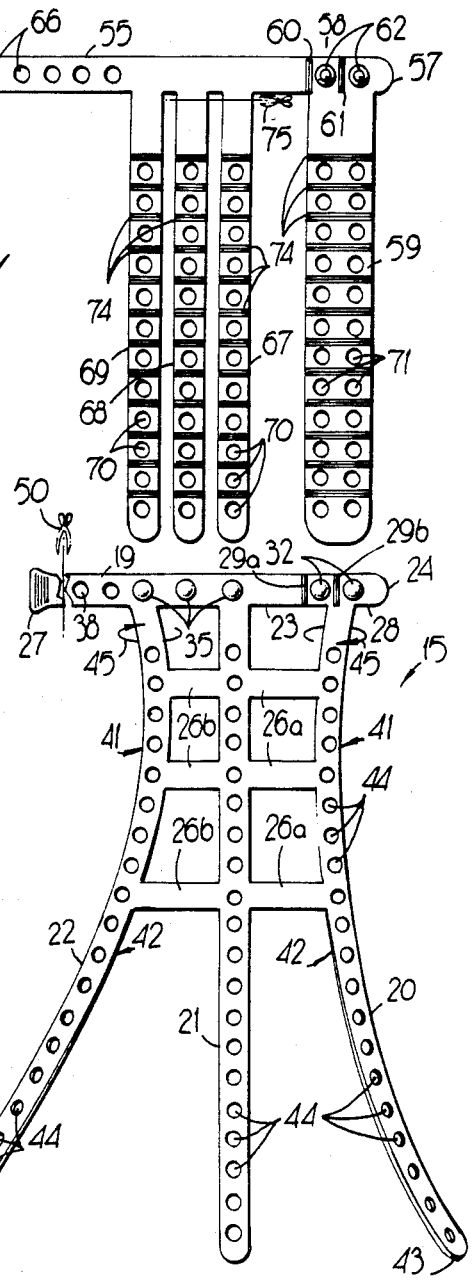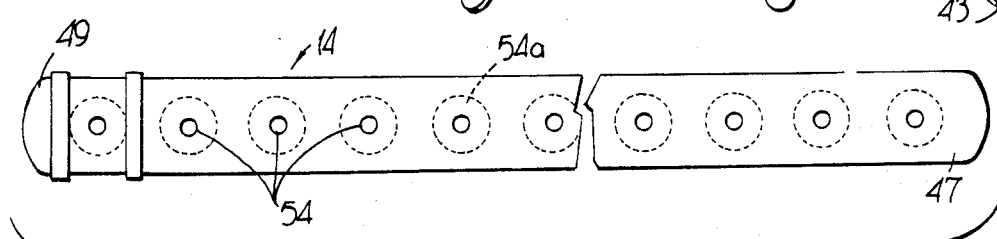

APPARATUS FOR INHIBITING DIGIT SUCKING

FIELD OF THE APPARATUS

This invention relates in general to preventing or inhibiting thumb and finger sucking, and in particular relates to such apparatus worn on the hand for preventing thumb and finger sucking.

BACKGROUND OF THE INVENTION

Thumb sucking and finger sucking are unsightly and unhealthy habits frequently adopted by children. Although these habits are extensions of the child's innate desire to suck, some children carry the habit well beyond the age when the child is weaned from or bottle-feeding. (Except where the context of usage indicates otherwise, the term "thumb sucking" is hereafter used to denote sucking one's thumb, index finger, or any other manual digit.)

Thumb sucking not only is unsightly, it also can have side effects deleterious to a person's health. For instance, any dirt or germs on the thumb sucker's hands becomes ingested into the body. When thumb sucking persists as the child begins teething, the constant presence of a thumb between the gums can deflect the incoming teeth from their normal positions in the jaw. When a thumb sucking problem persists through the arrival of permanent teeth, the result is crooked teeth which can be overcome only by expensive and time-consuming orthodontal treatment. Persistent thumb sucking at this stage also can abrade the skin on the thumb, leading to infection. Moreover, thumb sucking can produce emotional discomfort if the child is teased by his or her peers or scolded by adults for the activity.

Thumb sucking is a recognized problem, and various attempts to overcome this problem are known in the art. For example, one kind of solution proposes various dental applicances which fit in the roof of the thumb sucker's mouth. These appliances have prongs or other protrusions extending downwardly from the roof of the mouth, to prevent inserting one's thumb into the mouth. Such devices affect the speech of the wearer and can be very unpleasant, and the devices consequently are seldom used.

Another proposed technique for curing thumb sucking involves applying various bitter-tasting liquids to the thumb. The theory here is that the thumb sucker, associating a bitter or unpleasant taste with the act of thumb sucking, will stop sucking his or her thumb. The practical result, however, usually is that the thumb sucker washes his or her hands, removing the bitter taste for renewed thumb sucking.

Various anti-thumb sucking appliances for wearing on the user's hand also are known in the art. Examples are shown in U.S. Pats. Nos. 1,345,783 and 2,684,065. Such hand appliances generally have attempted to inhibit thumb sucking either by causing the wearer discomfort when attempting to insert thumb into mouth, or by preventing the thumb sucker from forming an airtight seal around the thumb and thus thwarting the sucking action craved by the child. However, anti-thumb sucking manual appliances of the art have been less than satisfactory. Such devices tend either to cover large portions of the hand, somewhat like a partial glove, or else fit in a relatively rigid unbending manner around a particular digit on the hand. In either case, these prior-art appliances greatly encumber the thumb sucker's hand and inhibit normal manual dexterity, so that anyone wearing the appliance has difficulty in drawing or writing, or undertaking other simple tasks requiring normal manual dexterity. As a result, such appliances of the prior art soon fall into disuse shortly after acquisition. Such devices also frequently are sold only in specific sizes, or are of a "one size fits all" nature which, in practice, means that one size seldom fits anyone particularly well. Anyone selling or fitting such appliances of the art thus must maintain an inventory of various-sized devices, to fit the hands of children at different ages and undergoing various rates of growth.

SUMMARY OF THE INVENTION

Stated in general terms, the anti-thumb sucking apparatus of the present invention fits around the wrist on the hand of a wearer and includes at least one ring encircling a digit on that hand. The apparatus preferably includes a wrist-encircling bracelet and tabs adjustably extending from the ring, locating the ring at a selected position on the digit. These elements are separately adjustable to fit the wrist and thumb or finger of the particular wearer.

Stated somewhat more particularly, the digit-engaging elements of the present invention include a primary ring adjustable to encircle an intermediate part of the wearer's thumb or finger. A separate booster ring attaches to the primary ring and encircles another location on the thumb or finger, especially an outer or end location. Spacer elements, such as tabs or bands extending lengthwise along the digit, keep the booster ring positioned with the selected amount of separation from the primary ring. The booster ring is optionally used on the thumb to control particularly advanced thumb suckers, and is required in adapting the present invention to finger suckers.

Stated in greater detail, the primary ring of the present invention is supported outwardly from an adjustable band or bracelet encircling the wrist. A tab attaches to the band and extends laterally therefrom, extending outwardly from the band along the inside or palm of the hand and lying generally parallel to the thumb or fingers when extended out from the hand. This tab preferably is flexible yet realtively inelastic, and maintains a predetermined shape while freely flexing with normal movements of the hand. At least one other tab also attaches to the wrist-encircling bracelet and extends laterally therefrom to lie alongside the back side of a selected digit on the hand. This additional tab or tabs, for example, can comprise a pair of tabs flanking the wearer's thumb along the back side thereof. These additional tab or tabs are spaced apart from each other, and collectively are spaced apart from the first-mentioned tab to locate the additional tabs on the back of the hand. These additional tabs can be laterally interconnected to prevent the wearer from slipping the heel or knuckle of the thumb out of the primary ring portion of the apparatus.

The digit-encircling elements comprise elongate members flexibly bendable to encircle the thumb or other digit of the hand. The interconnecting tabs likewise comprise flexible and preferably inelastic strap members extending downwardly from the digit-encircling members, for adjustable connection to the primary ring or the wrist bracelet. The interconnection between these respective tabs preferably is adjustable, and is selected to maintain the digit encircling members at the intermediate or outer ends of the digit.

Accordingly, it is an object of the present invention to provide improved apparatus for inhibiting or preventing thumb sucking.

It is another object of the present invention to provide an improved anti-thumb sucking apparatus for fitting on a user's hand.

It is yet another object of the present invention to provide apparatus for fitting on a hand to inhibit thumb sucking, while permitting manual manipulation of the hand for many purposes.

It is a further object of the present invention to provide anti-thumb sucking apparatus optionally including separate digit-encircling elements.

Other objects and advantages of the present invention will become more readily apparent from the following description of a preferred embodiment.

BRIEF DESCRIPTION OF DRAWINGS

FIG. 1 is a pictorial view showing anti-thumb sucking apparatus according to a preferred embodiment of the present invention, mounted on the thumb of a left hand shown in phantom outline.

FIG. 2 is a plan view of the apparatus depicted in FIG. 1, shown removed from the hand and disconnected to demonstrate the plane configuration of the elements comprising the embodiment.

FIG. 3 is a pictorial view of the apparatus shown in FIG. 1, with the elements separated and exploded.

FIG. 4 is a pictorial view showing the apparatus of FIG. 1 adapted to fit on a person's index finger.

FIG. 4A is a side view of the securing button interconnecting the wrist bracelet and primary ring attachment shown in FIGS. 1–3.

FIG. 5 is a fragmentary elevation view showing a portion of the primary ring.

DESCRIPTION OF PREFERRED EMBODIMENT

An anti-thumb sucking device embodying the present invention is shown generally at 10 in FIGS. 1 and 3. This device 10 is illustrated as worn on the thumb 11 of a wearer's hand, in FIG. 1. As will become apparent from the following description, however, the device 10 can easily be adapted to fit on another digit of the hand, for example, on the index finger 12 shown in FIG. 3 or any of the other fingers.

The anti-thumb sucking device 10 has three parts, including the wrist-encircling bracelet 14. The other two parts are the primary ring attachment 15 and related tabs connecting to the wrist bracelet 14, and the booster ring attachment 16 which connects to the primary ring 15. The booster ring 16, as pointed out below, includes another thumb-encircling ring and depending tabs, and is selectively attached to the primary ring 15. The booster ring 16 may not be necessary for less severe cases of thumb sucking.

Both the primary thumb-engaging ring 15 and the booster ring 16 in the disclosed embodiment are fabricated as unitary devices that can be stamped or otherwise formed from a single sheet of material, if desired. FIG. 2 shows the flat configuration of the primary ring 15 and booster ring 16, respectively aligned above the bracelet 14. Considering first the primary ring 15, this ring includes an elongated straight band 19 having three tabs 20, 21, and 22 extending laterally out from one side 23 of the band. The first of these tabs 20 joins the band 19 adjacent the first end 24 of the band. The other two tabs 22 and 23 are spaced apart from each other and from the first tab 20, along the length of the band 19. The tabs 20, 21, and 22 are linked together by three cross tabs 26a and 26b extending laterally between the tabs 20 and 21, and 21 and 22, and parallel to the band 19.

The other end 27 of the band 19 is slightly enlarged and thickened relative to the remainder of the band, to facilitate gripping the other end. The end 27 can be provided with a series of small vertical ridges to enhance gripping that end, if desired. The bank 19 forms the thumb-encircling ring 18, and the length of the band preferably is selected to be somewhat greter than the maximum circumference expected to be encompassed by the hand.

A relatively short segment 28 at the first end 24 of the band 19 is defined by the lateral groove 29 formed in the band immediately to the left of the first tab 20 and the lateral groove 29b between tab 21 and tab 20. The grooves 29a and 29b extend part way through the thickness of the band 19, leaving the remaining material of the band to form an integral hinge so that the band segment 28 can lie substantially flat on the inside of the thumb 11 while the remainder of the band bends around to form the first ring 18, shown in FIGS. 1 and 3.

A pair of longitudinally-spaced buttons 30 are permanently mounted in the end segment 28 of the band 19, preferably flanking the groove 29b which bisects the end segment. These buttons 30 have a first or inner lip 31 projecting outwardly a short distance from the outer face of the segment, and a second or outer lip 32 projecting a short distance formally from the first lip, as best seen in FIG. 5. The other ends of the buttons 30 are flush with the thumb-contacting surface 33 of the segment 28, to avoid causing trauma to the thumb. As best seen in FIG. 2, the two buttons 30 are longitudinally disposed on the tab segment 28 on opposite sides of the point where the first tab 20 laterally extends from the segment. The buttons 30 provide attachement points for connecting the booster ring 16 to the primary ring 15, as explained below.

The second tab 21 joins the band 19 a short distance to the left of the groove 29 in the band, as best seen in FIG. 2. The third tab 22, in turn, joins the band 19 a short distance spaced leftwardly of the second band 21. Three buttons 35, each having only a single outer lip similar to the lip 31 on buttons 30 but otherwise similar in shape and purpose to the buttons 30, protrude from the band 19 in the region between the second and third tabs 21 and 22.

The spacing between the second and third tabs 21 and 22, as well as the locations of those two tabs along the band 19, becomes apparent from FIGS. 1 and 2. thus, the tabs 21 and 22 lie along the back side of the thumb 11, and these two tabs preferably flank the back side of the thumb. The cross tabs 26a and 26b, extending between the tabs 21 and 22, fit around and loosely engage the heel region of the thumb and subjacent portions of the wearer's hand. Only one cross tab 26a and one cross tab 26b nearest band 19 will be left intact for a relatively small hand. The other four cross tabs should be cut off. For a medium sized hand two cross tabs 26a and two cross tabs 26b can be left. On bigger hands all three cross tabs 26a and 26b can be left as pictured, when the primary ring is engaged on the thumb. Fig. 1 also shows that the first tab 20 lies generally along the inner surface 37 of the thumb, extending downwardly from the knuckle joint and across the palm to join the wrist bracelet 14.

A number of holes 38 are formed through the band 19, along a band region to the left of the third tab 22 and extending approximately to the other end 27 of the band. The holes 38 are dimensioned to provide a snug engaging fit with the inner lips 31 of the buttons 30 disposed on the segment 28 adjacent the first end 24 of the band. As can be seen in FIGS. 1 and 3, the ring 18 is formed by looping the end 27 of the band 19 around the first end 24, with the wearer's thumb 11 in place within the loop. The loop thus formed should be a snug yet comfortable fit on the thumb. The two buttons 30 then are pressed through the corresponding pair of holes 38 which most nearly maintains the desired size of the ring 18; the inner lips 31 of the buttons engage two holes and secure the band 19 to maintain the ring. The two buttons 30 are very difficult to pull loose from the ring once secured. The thumb-engaging ring apparatus 15 thus is dimensioned to fit the thumb 11 of the user.

Returning to FIG. 2, it is seen that the first tab 20 and the third tab 22 both have an extent of curvature along their lengths, while the second tab 21 is substantially straight in the disclosed embodiment. For example, the upper end of the first tab 20 flares inwardly toward the second tab 21, as shown at 41 appoximately one-third the length of the first tab downwardly from the band 19, and then curves outwardly as at 42 to terminate at the other end 43. The third tab 22, as it extends downwardly fromthe band 19, likewise curves inwardly toward the second tab 21 and then curves back out to terminate at its lower end. The tabs 20, 21, and 22 each have a series of openings 44 therein, preferably commencing at the outer ends of the tabs and extending upwardly along at least a substantial portion of the tab lengths. These openings 44 have a slight bevel or chamfer on the tab side facing the hand, and the openings facilitate securing the tabs to the wrist band 14 as described below.

The upper ends of the first tab 20 and third tab 22 also have an extent of angular twist, indicated on FIG. 2 at 45, where theset abs join the band 19. The purpose of this angular twist 45, which in the preferred embodiment is approximately 30°, is explained below.

The operation of the apparatus is now considered, with initial reference only to the thumb-engaging ring 15. The wrist bracelet 14 first is positioned around the wearer's wrist immediately below the lower end of the hand 48, as shown in FIG. 1, and secured in place with the buckle 49 or other fastener. The thumb-engaging ring apparatus 15 is disconnected from the wrist band 14 at this time. The wrist bracelet 14 preferably is fabricated of a soft and pliable inelastic material, and this wrist bracelet should be relatively wider than the tabs and bands making up the ring 15 for added comfort on the wrist of the wearer.

The primary ring 15 now is fitted to the wearer's thumb 11. In the manner previously described, the band 19 is placed around the thumb 11, with the segment 28 of the band positioned on the front of the thumb approximately at the knuckle joint. After sizing the band 19 to form the ring 18 of desired diameter, the two buttons 30 are pressed through a corresponding pair of holes 38 in the tab, and the unneeded remainder of the band may be cut off and discarded as indicated by the scissors 50 in FIG. 2. With the ring 18 sized to fit the wearer's thumb 11, the primary ring apparatus 15 now is attached to the wrist bracelet 14. This is accomplished by extending the first tab 20 downwardly along the inner side of the wearer's thumb and wrist as shown in FIG. 1, to a point where the outer end 43 of the first tab overlaps the wrist bracelet. The first tab 20 is secured to the wrist bracelet 14 at this location by a suitable fastening device such as the securing button 51 or the like. As shown in FIG. 4A, the buttons 51 may have an enlarged head 52 for permanently interconnecting the tabs 20...22 to the wrist bracelet. The tab 21 will always attach between the two straps of the buckle 49 of the wrist bracelet 14 as shown in FIG. 1. The button 51a extending through the end flap 47 of the wrist bracelet has a relatively longer shank between the beveled base 53 (FIG. 4A) and the underside of the button head 52 to compensate for the double thickness of the bracelet. The base 53 of each button 51 is beveled to mate the chamfered inner surface 54a (FIG. 4) of the holes 54 in the bracelet 14. The buttons 51 and 51a are very difficult to remove from both the wrist bracelet 14 and the tabs 20 . . . 22.

The second tab 21 and third tab 22 are secured to the wrist bracelet 14 in similar fashion. As previously mentioned, these latter two tabs flank the back side of the wearer's thumb 11, and the length of these tabs should be adjusted so that the wearer can extend the thumb straight out in the usual manner. The flexibility of the tabs 20-22 thus permits the wearer to flex or bend the thumb without substantial impairment by the presence of the primary ring assembly 15. However, the second and third tabs 21 and 22, and particularly the cross tabs 26a and 26b extending between those two tabs, prevent the wearer from escaping the primary ring assembly 15 by moving the thumb downwardly within the ring 18 and then working the back of the thumb out between the tabs 21 and 22.

The purpose of the previously-mentioned inward and outward curvatures of the first tab 20 and the second tab 22 should now be more readily apparent. As seen in FIG. 1, these two tabs flare outwardly at the upper and lower ends to accommodate the natural contour of the hand and thumb, particularly when the thumb is fully extended as shown in that figure. At the same time, the inward curvature of the tabs 20 and 22, as shown at 41, helps contain the thumb within the primary ring apparatus 15 as the wearer flexes the thumb. The angular twist 45 of the tabs 20 and 22 help the bands lie substantially flat on the hand. The booster ring 16 is an optional attachment for the primary thumb-engaging ring 15, where the primary ring alone fails to inhibit a persistent thumb sucking habit. The booster ring 16 is a separate element fromt he primary ring 15, and is selectively attachable to the primary ring. The booster ring 16 includes an elongated upper band 55 which is bendable back onto itself to form the thumb-encircling ring 56, FIGS. 1 and 3, fitted near the outer end of the thumb 11. The band 55 of the booster ring 16 thus structurally and functionally resembles the band 19 forming the ring 18 of the primary thumb-engaging ring 15.

The band 55 has at one end 57 an end segment 58 with a tab 59 laterally joining and depending downwardly from the end segment. As seen from FIG. 1, the tab 59 is positioned on the front or pad of the thumb 11, and so the width of this tab preferably is substantially greater than that of the other lateral tabs on the disclosed embodiment. the end segment 58 is joined to the remainder of the band 55 by the transverse V-groove 60 extending across the band just to the left of the tab 59. The groove 50 functions as a connecting hinge between the end segment 58 and the band 55, much as the grooves 29a and 29b function in the band 19 of the primary ring 15. Another lateral V-groove 61 may extend intermediate the length of the end segment 58, if desired for greater flexibility of the end segment. A pair of attachment buttons 62 are permanently secured in the end segment 58, flanking the second groove 61 if present. These attachment buttons need have only a single lip, similar to the first lip 31 on the buttons 30.

The band 55 is of length at least sufficient to wrap around the largest thumb 11 on which it is anticipated the booster ring 16 will be used, and preferably is somewhat longer than that largest dimension. The other end 65 of the band 55 preferably is enlarged to form a manual gripping member. A series of holes 66 are formed in the band 55, in position for mutual alignment with the two buttons 62 when the band is wrapped around itself to form the ring 56 as shown in FIG. 1.

Three separate tabs 67, 68, and 69 join the band 55 and extend laterally downwardly therefrom. Each of these tabs is slightly spaced apart from each other along the length of the band 55, and the tabs collectively are spaced apart from the tab 59 which rests on the ball or face of the wearer's thumb 11. The tabs 67, 68, and 69 each have an array of holes 70, each beveled or chamfered on its underside, spaced along the length of the tabs. As pointed out below, these holes 70 assist in attaching the booster ring 16 to the primary ring 15. The relatively wide tab 59 has two longitudinal rows of holes 71 for the same purpose. Because the tab 59 and the tabs 67–69 are intended to be cut to fit the particular user, these tabs preferably are segmented for ease and convenience of cutting. Segmenting is accomplished by providing a series of grooves 74 extending across the width of each tab 59 and 67–69 at intervals along the lengths of the tabs. The grooves 74 may be molded or otherwise formed in the tabs, and these grooves preferably are interspaced with the holes 70 and 71 along the tabs.

The entire booster ring 16 preferably is a unitary article, as is the primary ring 15, and each such ring can be stamped or otherwise formed from a single sheet of a suitable flexible and relatively inelastic material such as a plastic or the like. Alternatively, the several tabs 59 and 68–70 can be formed as separate members and attached to the band 55; similarly, the tabs 20–22 of the primary ring 15 can be separately formed and attached to the band 19 of the primary ring.

The booster ring 16 is used in the following way. Assuming the primary ring 15 and bracelet 14 previously are fitted and attached to the wearer's hand as shown in FIG. 1, the band 55 of the booster ring 16 is sized to form the ring 56 adjacent the outer end of the thumb 11. As seen in FIG. 1, the groove 60 permits a sharp bend or transition in the direction of the band, thereby keeping the tab 59 aligned against the front of the thumb 11. Once the proper diameter of the ring 60 is chosen, the two buttons 62 are pressed through a corresponding pair of holes 66 in the band 55 to secure the ring configuration of the band and the remaining length of the tab 55 is cut off. The cut end of the band 55 preferably terminates adjacent the groove 60, as seen in FIG. 1.

With the thumb end ring 56 thus formed, the booster r5ing 16 now is positioned over the thumb 11 with the tab 59 lying along the front or pad of the thumb. The ring 16 is adjusted along the length of the thumb to locate the proper lengthwise location positioning the ring 56 adjacent the outer end of the thumb. With this lengthwise position determined, the booster ring 16 now is secured in place by urging the two double-length buttons 30, on the segment 28 of the thumb ring 15, through the adjacent pair of holes 71 in the tab 59 of the booster ring. The second lips 32 of the buttons 30 extend out beyond the band 19 far enought to enter and engage the selected holes 71 in the tab 59. Once secured, the buttons 30 can be removed only with great difficulty. The buttons 30 and holes 71 preferably are configured so that the booster ring 16, after attachment to the primary ring 15, can be detached only with great difficulty so that the child cannot cause removal. The excess length of the tab 59 beyond the length appropriate for the particular thum 11 now is cut off, for example, along the groove 74 at the outer end of the tab segment containing the holes 71 secured by the buttons 30.

Securement of the booster ring 16 is completed by selecting a single one of the tabs 67–69 for securement to a corresponding one of the three buttons 35 along the band 19 of the wrist ring 15. The selected one of tabs 67–69 should place that tab on or near alignment with the center of the back of the thumb 11. For relatively big thumbs, the tab 69 is used and the remaining tabs 68 and 70 are cut off adjacent the band 55, as schematically illustrated by the scissors 75 in FIG. 2. For a medium-sized thumb 11, the center tab 68 is used and the outer tabs 69 and 70 are cut off; this usage is seen in FIG. 1. Likewise, the innermost tab 67 is used for a relatively small thumb and the outer two tabs 68 and 69 are cut off.

The remaining tab 68, in the disclosed explanation, extends downwardly and is aligned as seen in FIG. 2 with one of the buttons 35 attached to the band 19 of the thumb ring 15. This corresponding button 35 is pressed through the appropriate hole 70 in the remaining tab 68, and the remainder of the tab is cut off along the groove 74 immediately below that hole. Once the appropriate button 35 is snapped through the tab 68, it will be very difficut to pull the tab loose from the band 19.

The booster ring 16 now is supported on the outer portion of the thumb 11, as shown in FIG. 1, with the ring 56 proximate the outer end of the thumb. The wide tab 59 and the other tab 68 (or 67 or 70, depending on thumb size) support the bosoter ring 16 in place, using the primary ring 15 as a supporting foundation. The tabs 59 and 68 are substantially straight and join the band 55 at a right-andlge, unlike the tabs 20 and 22 of the primary ring 15, because the tabs of the booster ring all lie substantially parallel to the linear outer extent of the thumb 11. Once the booster ring 16 is sized to fit the thumb of a particular wearer, this booster ring can easily be attached to the primary ring 15 but can be removed therefrom only with great difficult.

FIG. 4 shows the disclosed embodiment adapted to fit the index finger 12 instead of the thumb. Both the primary ring 15 and the booster ring 16 must be used in this adaptation, placing the ring 18 approximately below the first knuckle joint 78 of the finger 16 and the ring 56 adjacent the finger tip.

With the finger-ring adaptation of the present apparatus, only two of the three tabs 20–22 on the primary ring 15 may be needed for users with relatively small hands. The first tab 20, attached to the segment 28 at the first end of the ring 18, is positioned to extend along the wearer's palm between the wrist band 14 and the outstretched finger 12. The relatively straight second tab 21 lies substantially along the back of the index finger 12 and the hand 48, connecting to the wrist bracelet 14 between the straps on the buckle 49 at approximately the opposite side thereof from the outer end 43 of the first tab 20. The third tab 22, unused inthe finger ring application of the disclosed embodiment, has been cut off the ring 15 and does not appear in FIG. 4. Likewise, the cross tabs 26a and 26b are unused in this application and have been cut off; the stubs of the cross tabs 26a and 26b in FIG. 4 are the vestigial remains of the cross tabs. The tab 21 for the finger-sucker adaptation should be angularly twisted in the same direction and extent as the twist 45 of tab 20, described previously, to help the tab 21 lie substantially flat on the back of the finger 12 and the hand.

For curing finger sucking in older children or those with relatively larger hands, all three tabs 20–22 of the primary ring 15 preferably are used. Even so, the three cross-tabs 26a should be cut off to permit adaptation to the finger. One or more of the cross tabs 26b shall (depending on the size of the hand) be left intact to prevent the knuckle at the base of the finger from escaping backwards, thus keeping the primary ring engaged.

The booster ring 16 is fitted to the index finger 12 in much the same way as previously described with respect to fitting on the thumb. Again, the tab 59 extends downwardly from the upper ring 55 and joins the lower ring 18 by means of the second outer lips 32 on the two buttons 30. The amount of tab 59 required to position the ring 55 adjacent the outer end of the index finger 12 is somewhat greater than required to fit the thumb 11. The tab 68, extending downwardly from the band 55 on the back of the index finger 12, likewise must be cut somewhat longer than in the thumb application shown in FIG. 1.

The apparatus just described is intended for use on the left hand of a wearer. It should be understood that right-hand embodiment is the mirror image of the described apparatus.

It will thus be seen that the present apparatus is easily adapted to fit the thumb or a finger of a particular wearer. Furthermore, the present apparatus can be sold in only one size, yet is quickly fitted to the thumb or finger of a particular user. The ring or rings surrounding the thumb, and also the tabs securing the respective rings in place, prevent or hinder the thumb sucker from obtaining the desired sucking action when the thumb is placed in the mouth. Moreover, the physical presence of the apparatus surrounding the thumb, while not harmful to the thumb sucker, is a foreign object and thus not conductive to keeping thumb in mouth. The substantial flexibility of the apparatus provides relatively little hindrance to normal wrist and hand movements, allowing the wearer to grasp and manipulate most objects as though the device were not present.

It should be understood that the foregoing relates only to a preferred embodiment of the present invention, and that numerous changes and modifications may be made therein without departing from the spirit and scope of the inention as defined in the following claims.

I claim:

1. Apparatus for inhibiting digit sucking, comprising:
    means encircling the wrist of a hand;
    primary digit encircling means attached to said wrist encircling means and extending outwardly therefrom to encircle an intermediate portion of a selected finger or thumb on the hand; and
    booster digit encircling means selectively connectable to said primary digit encircling means and extending further outwardly along the selected finger or thumb to encircle an outer portion thereof, whereby said booster digit encircling means can be selectively added to enhance the thumb sucking inhibiting effect of the apparatus;
    said primary digit encircling means comprising a flexible band of noncircular cross-section at least long enough to encircle said intermediate portion of the selected digit;

means joining said flexible band in substantially circular configuration to form a ring encircling said intermediate portion;
a first resilient tab joining said flexible band at a location thereon overlying the front side of the selected digit, said first tab extending laterally downwardly from the flexible band to said wrist encircling means along the front side of said digit and in generally parallel relation to said digit;
at least one other resilient tab joining said flexible band in spaced apart relation thereon from said first tab, said other tab extending downwardly from said flexible band to said wrist encircling means in generally parallel relation to said digit; and
means attaching said tabs to said wrist encircling means, so that the tabs maintain said flexible digit-encircling band at a predetermined distance apart from the wrist encircling means.

2. Apparatus as in claim 1, wherein:
said first tab joins an end portion of said flexible band; and further comprising
protruding means disposed at said end portion of the flexible band and protruding outwardly therefrom;
tab means associated with said bosoter digit encircling means and extending to overlap said end portion; and
opening means on said tab means for selective engagement with said protruding means, whereby said bosoter means is selectively connected to said primary digit encircling means.

3. Apparatus as in claim 1, further comprising
means defining an end portion adjacent one end of said flexible band;
securement means associated with said end portion and protruding radially outwardly therefrom;
a plurality of openings formed through said band at intervals therealong, said openings being selectively engagable with said securement means and spaced along the length of the band to define a range of digit-encircling sizes as the flexible band is fitted around said selected digit.

4. Apparatus as in claim 1, wherein:
said other tab is one of two other tabs joining said flexible band and extending downwardly to said wrist encircling means;
said other tabs being mutually spaced apart along the length of said flexible band at locations thereon placing said other tabs overlying the back of the selected digit while said first tab overlies the front side of said digit; and
means selectively attaching said other tabs to said wrist encircling means.

5. Apparatus as in claim 4, wherein:
one of said other tabs extends apprxoimately along the middle back of said selected digit, and the remaining said other tab and said first tab flank said one other tab on both sides thereof; and further comprising
at least one cross tab extending between and interconnecting said tabs at a location therealong behind the selected digit to prevent withdrawing the selected digit backward from between said tabs.

6. Apparatus as in claim 4 wherein
the intermediate one of said tabs is substantially straight and joins said flexible band at substantially a perpendicular thereto; and
the two tabs flanking said intermediate tab each are arcuate and join said flexible band at an acute angle thereto facing the intermediate tab, said flanking tabs moving closer to the intermediate tab as the distance down from said flexible band increases, and said flanking tabs then bending away from the intermediate tab for attachment to said wrist encircling means.

7. Apparatus as in claim 1, wherein:
said primary digit encircling means and said booster digit encircling means are flexible and substantially inelastic, and have a certain shape.

8. Apparatus as in claim 1, wherein said tabs are substantially inelastic and thereby maintain said digit-encircling band at a fixed distance from the wrist encircling means.

9. Apparatus for inhibiting digit sucking, comprising:
means encircling the wrist of a hand;
primary digit encircling means attached to said wrist encircling means and extending outwardly therefrom to encircle an intermediate portion of a selected finger or thumb on the hand; and
booster digit encircling means selectively connectable to said primary digit encircling means and extending further outwardly along the selectedfinger or thumb to encircle an outer portion thereof, whereby said booster digit encircling means can be selectively added to enhance the thumb sucking inhibiting effect of the apparatus;
said primary digit encircling means comprising a flexible band of noncircular cross-section at least long enough to encircle said intermediate portion of the selected digit;
means joining said flexible band in substantially circular configuration to form a ring encircling said intermediate portion;
a first tab joining said flexible band at a location thereon overlying the front side of the selected digit, and extending laterally downwardly from the flexible band to said wrist encircling means in generally parallel relation to said digit;
at least one other tab joining said flexible band in spaced apart relation thereon from said first tab, and extending downwardly to said wrist encircling means in generally parallel relation to said digit;
means attaching said tabs to said wrist encircling means, so that the tabs maintain said flexible digit-encircling means;
means providing a region of increased flexibility across a predetermined location on said flexible band and thereby allowing a selected portion of said band to conform to the encircled digit independently to the remainder of said band; and
said first tab joining said band at said selected portion thereof, so that the selected portion overlies the front of said digit, allowing the remainder of the band to encircle the digit behind the front portion thereof.

10. Apparatus for inhibiting digit sucking, comprising:
means encircling the wrist of a hand;
primary digit encircling means attached to said wrist encircling means and extending outwardly therefromto encircle an intermediate portion of a selected finger or thumb on the hand; and
booster digit encircling means selectively connectable to said primary digit encircling means and extending further outwardly along the selected finger or thumb to encircle and outer portion thereof, whereby said booster digit encircling means can be selectively added to enhance the thumb cuking inhibiting effect of the apparatus;

said primary digit encircling means comprising a first flexible band of noncircular cross-section at least long enough to encircle said intermediate portion of the selected digit;

means joining said first flexible band in substantially circular configuration to form a ring encircling said intermediate portion;

a first tab joining said flexible band at a location thereon overlying the front side of the selected digit, and extending laterally downwardly from the flexible band to said wrist encircling means in generally parallel relation to said digit;

at least one other tab joining said flexible band in spaced apart relation thereon from said first tab, and extending downwardly to said wrist encircling means in generally parallel relation to said digit;

means attaching said tabs to said wrist encircling means, so that the tabs maintain said flexible digit-encircling band at a predetermined distance apart from the wrist encircling means;

said booster digit encircling means comprising a second flexible band at least long enough to encircle said outer portion of the selected digit;

a second tab joining said second band and extending downwardly therefrom along said front side of the selected digit to meet said first band at the location thereon joined by said first tab; and means detachably securing said second tab to said first band.

11. Apparatus as in claim 10, wherein:

said second tab comprises a plurality of discrete segments defined along the length of the second tab;

each said segment being defined by a weakened region extending across the width of the second tab, said second tab thus being especially flexible at the weakened regions; and apertures formed in the second tab in at least some of said segments, for interconnecting the second tab to said first band.

12. Apparatus for inhibiting digit sucking, comprising:

means encircling the wrist of a hand;

primary digit encircling means attached to said wrist encircling means and extending outwardly therefrom to encircle an intermediate portion of a selected finger or thumb on the hand; and booster digit encircling means selectively connectable to said primary digit encirclig means and extending further outwardly along the selected finger or thumb to encircle an outer portion thererof, whereby said booster digit encircling means can be selectively added to enhance the thumb sucking inhibiting effect of the apparatus;

said primary digit encircling means comprising a flexible band of noncircular cross-section at least long enough to encircle said intermediate portion of the selected digit;

means joining said flexible band in substantially circular configuration to form a ring encircling said intermediate portion;

a first tab joining said flexible band at a location thereon overlying the front side of the selected digit, and extending laterally downwardly from the flexible band to said wrist encircling means in generally parallel relation to said digit;

at least one other tab joining said flexible band in spaced apart relation thereon from said first tab, and extending downwardly to said wrist encircling means in generally parallel relation to said digit;

means attaching said tabs to said wrist encircling means, so that the tab maintain said flexible digit-encircling band at a predetermined distance apart from the wrist encircling means;

means defining an end portion adjacent one end of said flexible band;

securement means associated with said end portion and protruding outwardly therefrom;

a plurality of openings formed in said band at intervals therealong, said penings being selectively engagable with said securement means and spaced along the length of the band to define a range of digit-encircling sizes as the flexible band is fitted around said selected digit;

tab means associated with said booster digit-encircling means and extending in approximately parallel relation along said selected digit to overlap said end portion of said flexible band; and at least one opening forming in said tab means;

whereby said tab means opening selectively engages said securement means associated with said end portion and thereby maintains said booster means in predetermined relation to said primary means on the selected digit.

13. Apparatus for inhibiting digit sucking, comprising:

means encircling the wrist of a hand;

primary digit encircling means attached to said wrist encircling means and extending outwardly therefrom to encircle an intermediate portion of a selected finger or thumb on the hand; and booster digit encircling means selectively connectable to said primary digit encircling means and extending further outwardly along the selected finger or thumb to encircle an outer portion thereof, whereby said bosoter digit encircling means can be selectively added to enhance the thumb sucking inhibiting effect of the apparatus;

said primary digit encircling means comprising a flexible band at least long enough to encircle said intermediate portion of the selected digit;

a first tab joining said flexible band at a location thereon overlying the front side of the selected digit, said first tab extending laterally downwardly from the flexible band to said wrist encircling means in generally parallel relation to said digit;

at least one other tab joining said flexible band in spaced apart relation from said first tab, said other tab extending downwardly from said flexible band to said wrist encircling means in spaced apart relation to said first tab and in generally prallel relation to said digit;

means attaching said tabs to said wrist encircling means so that the tabs flank said digit and maintain said flexible digit-encircling band at a predetermined distance apart from the wrist encircling means; and at least one cross tab extending between and interconnecting said tabs at a location therealong behind said digit, thereby preventing withdrawing the digit backward form between the tabs flanking the digit.

* * * * *